United States Patent
Suzuki et al.

(10) Patent No.: US 11,040,182 B2
(45) Date of Patent: Jun. 22, 2021

(54) MICRONEEDLE DEVICE AND METHODS

(71) Applicant: NOVEN PHARMACEUTICALS, INC., Miami, FL (US)

(72) Inventors: Masayuki Suzuki, Miami, FL (US); Cormac H. Lyons, Miami, FL (US)

(73) Assignee: NOVEN PHARMACEUTICALS, INC., Miami, FL (US)

( * ) Notice: Subject to any disclaimer, the term of this patent is extended or adjusted under 35 U.S.C. 154(b) by 0 days.

(21) Appl. No.: 14/827,735

(22) Filed: Aug. 17, 2015

(65) Prior Publication Data
US 2016/0045720 A1 Feb. 18, 2016

Related U.S. Application Data

(60) Provisional application No. 62/038,538, filed on Aug. 18, 2014.

(51) Int. Cl.
*A61M 37/00* (2006.01)
*B29K 105/00* (2006.01)
*B29L 31/00* (2006.01)
*B29C 35/08* (2006.01)

(52) U.S. Cl.
CPC . *A61M 37/0015* (2013.01); *A61M 2037/0046* (2013.01); *A61M 2037/0053* (2013.01); *A61M 2037/0061* (2013.01); *A61M 2205/02* (2013.01); *A61M 2205/0238* (2013.01); *A61M 2205/0244* (2013.01); *A61M 2205/0283* (2013.01); *B29C 2035/0822* (2013.01); *B29C 2035/0827* (2013.01); *B29C 2035/0855* (2013.01); *B29C 2035/0877* (2013.01); *B29K 2039/06* (2013.01); *B29K 2105/0035* (2013.01); *B29K 2105/0038* (2013.01); *B29L 2031/753* (2013.01)

(58) Field of Classification Search
None
See application file for complete search history.

(56) References Cited

U.S. PATENT DOCUMENTS

| | | | | |
|---|---|---|---|---|
| 2007/0083147 | A1* | 4/2007 | Smith | A61N 1/30 604/20 |
| 2008/0153795 | A1* | 6/2008 | Occleston | A61K 31/56 514/182 |
| 2009/0131905 | A1* | 5/2009 | Allen | A61B 5/14514 604/501 |
| 2010/0256064 | A1* | 10/2010 | Woolfson | A61B 17/205 514/15.2 |
| 2011/0112509 | A1* | 5/2011 | Nozaki | A61B 17/205 604/506 |
| 2011/0195124 | A1* | 8/2011 | Jin | A61K 9/0021 424/486 |
| 2015/0080802 | A1* | 3/2015 | Kang | G03F 7/2002 604/173 |

* cited by examiner

Primary Examiner — Robert A Wax
Assistant Examiner — Quanglong N Truong
(74) Attorney, Agent, or Firm — Foley & Lardner LLP

(57) ABSTRACT

Described are microneedle devices comprising an electron beam crosslinked or photocrosslinked polymer material, and methods of making and using them, such as for drug delivery or sampling biological fluids.

37 Claims, 4 Drawing Sheets

MICRONEEDLE DEVICE AND METHODS

This application claims the benefit of priority to U.S. Provisional Patent Application No. 62/038,538, filed on Aug. 18, 2014, which is incorporated by reference herein in its entirety.

FIELD

The present disclosure generally relates to microneedle devices, more specifically to microneedle devices comprising an electron beam crosslinked or photocrosslinked polymer material, and methods of making and using them.

BACKGROUND

Microneedle devices have been used for transdermal drug delivery, and for sampling analytes or biomarkers. Typically, microneedle devices are placed on the skin surface such that the microneedles pierce the stratum corneum (the outermost layer of the skin) facilitating drug delivery or sampling of biological fluids (e.g., blood). With regard to drug delivery, current microneedle technologies typically provide bolus dosing with pharmacokinetic profiles similar to that observed with subcutaneous injection.

Dissolvable polyvinylpyrrolidone (PVP) microneedles for vaccine delivery have been reported. See, e.g., K. A. Moga et al., "Rapidly-Dissolvable Microneedle Patches Via a Highly Scalable and Reproducible Soft Lithography Approach," *Adv. Materials* 25: 5060-66 (Sep. 25, 2013); L. Guo et al., "Enhanced transcutaneous immunization via dissolving microneedle array loaded with liposome encapsulated antigen and adjuvant," *Int'l J. Pharmaceutics* 447: 22-30 (Apr. 15, 2013); W. Sun et al., "Polyvinylpyrrolidone microneedles enable delivery of intact proteins for diagnostic and therapeutic applications," *Acta Biomaterialia* 9: 7767-74 (May 3, 2013). The materials used for these microneedles are not crosslinked, and the microneedle devices yield pharmacokinetic profiles similar to that observed with subcutaneous injection.

Microneedles comprised of blends of polymethylvinylether/maelic acid and polyethyleneglycol crosslinked via esterification reactions with heating at 80° C. for 24 hours also have been reported. See R. F. Donnelly et al, "Hydrogel-Forming Microneedle Arrays for Enhanced Transdermal Drug Delivery," *Adv. Functional Materials* 22: 4879-90 (2012). Microneedles formed using organic solvent as polymer catalysts also have been reported, wherein the organic solvent is removed by washing after fabrication. See S. Y. Yang, "A bio-inspired swellable microneedle adhesive for mechanical interlocking with tissue," *Nature Communications* 4: 1702 (Apr. 16, 2013). However, chemical and physical crosslinking requires the use of chemical and physical crosslinking agents, such as peroxides, vinylsilanes, triethanolamine, bisacrylamide, polycarboxylic acids, halogenated dicarboxylic acids, polycarboxylic anhydrides, aldehyde compounds, N-methylol compounds, metaphosphoric acid salts, divinyl compounds, bis-aziridine, ethylene-vinyl acetate, isocyanate compounds, aluminum hydroxide, silanol compounds, epoxy compounds, melamine compounds, carbodimide compounds, hydrazide compounds, ester compounds, and epichlorohydrin, or the like. The use of such materials in microneedle is disadvantageous because, for example, some of these materials are irritants to the skin, eyes, and respiratory tract, while others may be allergens, or may be otherwise toxic or carcinogenic. Additionally, such crosslinking agents can interact with the drug(s) being delivered or the analyte(s) or biomarker(s) being sampled, and can cause systemic delivery problems. See, e.g., J. Sekizawa, "A simple method for screening assessment of skin and eye irritation," *F. Toxicological Sciences* 19: 25-35 (2008).

Thus, there remains a need for microneedle devices that can be formed without the use of chemical and physical crosslinking agents and that can provide sustained drug delivery.

SUMMARY

In some embodiments, there are provided a microneedle device comprising an array of a plurality of microneedles, wherein the microneedles comprise an electron beam crosslinked or photocrosslinked polymer material. In some embodiments, the electron beam crosslinked or photocrosslinked polymer material is a hydrogel material. In specific embodiments, the electron beam crosslinked or photocrosslinked polymer material comprises one or more materials selected from the group consisting of polyvinylpyrrolidone (PVP), polyethylene oxide, polyvinylalchol, polyacrylamide, poly(N-isopropylacrylamide) or its copolymers, dextran, pullulan, chitosan, gelatin, sodium alginate, cellulose, hydroxypropylcellulose, hydroxypropylmethylcellulose, hydroxyethylcellulose, carboxymethylcellulose, silk polymer, amylopectin, chondroitin sulfate, poly(lactic-co-glycolic acid), fibrin, elastin, collagen, hyaluronic acid, functionalized or modified above polymers, and mixtures and blends of two or more thereof. In further specific embodiments, the electron beam crosslinked or photocrosslinked polymer material comprises PVP. In some embodiments, the electron beam crosslinked or photocrosslinked polymer material further comprises a plasticizer, such as one or more plasticizers selected from the group consisting of polyethyleneglycol, liquid paraffin, dioctyl phthalate, diisononyl phthalate, diisodecyl phthalate, dibutyl phthalate, dioctyl adipate, diisononyl adipate, trioctyl trimellitate, tricresyl phosphate, acetyl tributyl citrate, epoxidized soybean-oil, epoxidized linseed-oil, sebacate.

In accordance with any of the foregoing embodiments, the array may be disposed on a backing member, such as a backing member in the form of a sheet comprising one or more materials selected from the group consisting of PVP, polyvinylalchol, pullulan, chitosan, gelatin, sodium alginate, cellulose, polyacrylamide, poly(N-isopropylacrylamide) or its copolymers, hydroxypropylcellulose, hydroxypropylmethylcellulose, hydroxyethylcellulose, carboxymethylcellulose, silk polymer, amylopectin, chondroitin sulfate, poly(lactic-co-glycolic acid), fibrin, elastin, collagen, hyaluronic acid, dextran, functionalized or modified above polymers, and mixtures or blends of two or more thereof. In some embodiments, the backing member is in the form of a flexible mesh membrane comprising one or more materials selected from the group consisting of nylon, polypropylene, stainless steel, ethylene-vinyl acetate, polyethylene terephthalate, polyurethane, woven or non-woven fabric. In accordance with any of these embodiments, the array may be disposed on the backing member such that the backing member comprises a peripheral border region that does not comprise microneedles. In some embodiments, at least a portion of the peripheral border region is provided with an adhesive, which optionally may be provided with a release liner overlaying the adhesive.

In accordance with any of the foregoing embodiments, the microneedles may dissolve in water or may swell in water.

In accordance with any of the foregoing embodiments, the electron beam crosslinked or photocrosslinked polymer material may further comprise a drug.

In accordance with any of the foregoing embodiments, the device may further comprise a drug-containing composition applied to one or more of an exterior or interior surface of the microneedles and/or on a face of the device. In some embodiments, the device has a front face from which the microneedles protrude and a back face opposite the front face, and further comprises a flexible, finite transdermal drug delivery system or a drug-containing semi-solid, liquid, gel, ointment or emulsion composition disposed on the back face.

In accordance with any of the foregoing embodiments, the electron beam crosslinked or photocrosslinked polymer material further comprises a drug and a drug-containing composition is applied to one or more of an exterior or interior surface of the microneedles and/or on a face of the device. In such embodiments, the drug included in the electron beam crosslinked or photocrosslinked polymer material may be the same or different from the drug in the drug-containing composition.

In accordance with any of the foregoing embodiments, the device may provide sustained delivery of the drug over a period of time selected from the group consisting of at least 1 hour, at least 2 hours, at least 3 hours, at least 4 hours, at least 6 hours, at least 8 hours, at least 12 hours, at least 24 hours, at least 30 hours, at least 36 hours, and at least 72 hours.

Also provided are methods of making a microneedle device comprising forming an intermediate microneedle array structure from a solution comprising an electron beam crosslinkable or photocrosslinkable polymer material and irradiating the intermediate microneedle array structure with electron beam, ultraviolet, infrared, or microwave radiation to induce crosslinking of the electron beam crosslinkable or photocrosslinkable polymer material. In some embodiments, the electron beam crosslinkable or photocrosslinkable polymer material comprises one or more materials selected from the group consisting of polyvinylpyrrolidone (PVP), polyethylene oxide, polyvinylalchol, polyacrylamide, poly(N-isopropylacrylamide) or its copolymers, dextran, pullulan, chitosan, gelatin, sodium alginate, cellulose, hydroxypropylcellulose, hydroxypropylmethylcellulose, hydroxyethylcellulose, carboxymethylcellulose, silk polymer, amylopectin, chondroitin sulfate, poly(lactic-co-glycolic acid), fibrin, elastin, collagen, hyaluronic acid, functionalized or modified above polymers, and mixtures and blends of two or more thereof. In further specific embodiments, the electron beam crosslinked or photocrosslinked polymer material comprises PVP. In some embodiments, the electron beam crosslinked or photocrosslinked polymer material further comprises a plasticizer, such as one or more plasticizers selected from the group consisting of polyethyleneglycol, liquid paraffin, dioctyl phthalate, diisononyl phthalate, diisodecyl phthalate, dibutyl phthalate, dioctyl adipate, diisononyl adipate, trioctyl trimellitate, tricresyl phosphate, acetyl tributyl citrate, epoxidized soybean-oil, epoxidized linseed-oil, sebacate.

In some embodiments, the intermediate microneedle array structure is formed by a process selected from the group consisting of coating the solution into a mold, casting the solution in a mold, casting the solution into a sheet followed by embossing, extruding the solution into a sheet followed by embossing, and 3D printing.

In accordance with any of the foregoing embodiments, the method may further comprise a drying step before or after the irradiating step, and or may method further comprise, before or after the irradiating step, applying the microneedle array structure to a backing member.

In accordance with any of the foregoing embodiments, the irradiating step provides an absorbed radiation dose of from 10 to 600 kilograys, or at least 100 kilograys, or about 300 kilograys.

In accordance with any of the foregoing embodiments, the electron beam crosslinkable or photocrosslinkable polymer material may further comprise a drug. In accordance with any of the foregoing embodiments, the device has a front face from which the microneedles protrude and a back face opposite the front face, and the method further comprises applying a flexible, finite transdermal drug delivery system or a semi-solid, liquid, gel, ointment or emulsion drug-containing composition to the back face.

Also provided are methods of delivering a drug to a subject in need thereof comprises applying one or more of the microneedle devices described herein to the skin of the subject, and uses of the microneedle devices described herein in methods of delivering a drug to a subject in need thereof for treatment or prophylaxis.

Also provided are methods of sampling a biological fluid from a subject comprising applying one or more of the microneedle devices described herein to the skin of the subject, and uses of the microneedle devices described herein in methods of sampling a biological fluid from a subject.

DETAILED DESCRIPTION

Figure 1:
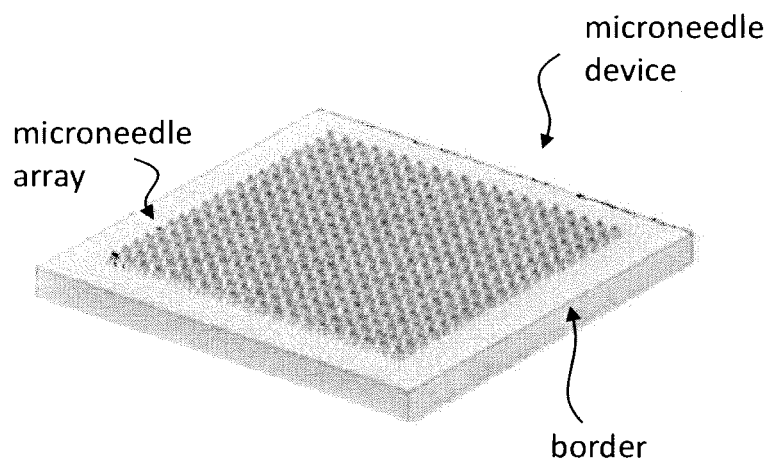
FIG. 1 is a front, top perspective view of a microneedle device according to a first embodiment described herein.

Described herein are microneedle devices comprising electron beam crosslinked or photocrosslinked polymer material, and methods of making and using them. The microneedle devices can be designed to dissolve or swell in water and provide sustained transdermal drug delivery.

Definitions

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The phrase "substantially free" as used herein generally means that the described material (e.g., transdermal drug delivery system, polymer, microneedle, etc.) comprises less than about 5%, less than about 3%, or less than about 1% by weight, based on the total weight of the material at issue, of the excluded component. The phrase "free of" as used herein means that the described material (e.g., polymer, microneedle, etc.) is formed without adding the excluded component(s) as an intended component, although trace amounts may be present, such as being a by-product or contaminant, such that the material comprises at most only trace amounts of the excluded component(s).

As used herein "subject" denotes any animal in need of drug therapy or biological fluid sampling, including humans. For example, a subject may be suffering from or at risk of developing a condition that can be treated or prevented with a drug, or may be taking a drug for health maintenance purposes, or may be having a biological fluid sample taken for diagnostic, therapeutic or health maintenance purposes.

As used herein, the phrases "therapeutically effective amount" and "therapeutic level" mean that drug dosage or plasma concentration in a subject, respectively, that provides the specific pharmacological response for which the drug is administered to a subject in need of such treatment, for whatever reason. It is emphasized that a therapeutically effective amount or therapeutic level of a drug will not always be effective in treating the target conditions/diseases, even though such dosage is deemed to be a therapeutically effective amount by those of skill in the art. For illustration only, exemplary dosages, drug delivery amounts, therapeutically effective amounts and therapeutic levels are provided below with reference to adult human subjects. Those skilled in the art can adjust such amounts in accordance with standard practices as needed to treat a specific subject and/or condition/disease.

In the following description, for purposes of explanation and not limitation, details and specific embodiments are set forth in order to provide a thorough understanding of the invention. It will be apparent to those skilled in the art that the invention may be practiced in other embodiments that depart from the details and specific embodiments.

Microneedle Devices

Described herein are microneedle devices comprising an array of a plurality of microneedles, wherein the microneedles are formed from an electron beam crosslinked or photocrosslinked (e.g., ultraviolet, infrared, or microwave crosslinked) polymer material. The microneedle devices can be designed to dissolve or swell in water and provide sustained transdermal drug delivery.

The polymer material use to form the microneedles may be any polymer material suitable for such use, such as any polymer material that can be crosslinked by electron beam or photo-irradiation, such as ultraviolet, infrared, or microwave irradiation, and that is suitable for use as a microneedle (e.g., that is non-toxic or otherwise acceptable for insertion into the skin). In specific embodiments, the polymer material comprises a hydrogel material. In further specific embodiments, the polymer material comprises polyvinylpyrrolidone (PVP). PVP has an established safety profile and is used in many pharmaceutical contexts, including as a drug excipient, as a plasma substitute, and in wound dressings. Other suitable polymer materials include polyethylene oxide, polyvinylalchol, polyacrylamide, poly(N-isopropylacrylamide) or its copolymers, dextran, pullulan, chitosan, gelatin, sodium alginate, cellulose, hydroxypropylcellulose, hydroxypropylmethylcellulose, hydroxyethylcellulose, carboxymethylcellulose, silk polymer, amylopectin, chondroitin sulfate, poly(lactic-co-glycolic acid), fibrin, elastin, collagen, hyaluronic acid, functionalized or modified species of the above polymers, and mixtures or blends of any two or more of the above polymers. In further specific embodiments, the polymer material further comprises a plasticizer. The plasticizer may be any plasticizer suitable for such use, such as polyethyleneglycol, liquid paraffin, dioctyl phthalate, diisononyl phthalate, diisodecyl phthalate, dibutyl phthalate, dioctyl adipate, diisononyl adipate, trioctyl trimellitate, tricresyl phosphate, acetyl tributyl citrate, epoxidized soybean-oil, epoxidized linseed-oil, sebacate, or mixtures or blends of two or more thereof.

Methods of making the microneedles described herein are described in more detail below. Generally, the methods include forming an intermediate microneedle array structure from the polymer material and treating the formed intermediate microneedle array structure with electron beam or photo-irradiation, such as ultraviolet, infrared, or microwave irradiation. As discussed in more detail below, such irradiation crosslinks the polymer material and also may serve to sterilize the microneedles.

As discussed below and illustrated in the examples, in some embodiments the extent of polymer crosslinking is selected and controlled to select and control of whether the microneedles dissolve or swell, and to impact the strength and hardness of the microneedles. For example, exposure to moisture (e.g., water) present in the interstitial fluid and/or in any drug-containing composition used in conjunction with the microneedles may lead to swelling or dissolution of the microneedles, depending on the characteristics of the microneedles. As discussed in more detail below, the extent of crosslinking and dissolvability vs. swellability also may impact drug delivery, e.g., the rate at which drug diffuses from the device.

In accordance with any of the embodiments of microneedles described herein, the array of a plurality of microneedles may be disposed on a backing member. The backing member may be integrally formed with the microneedles and may be comprised of the same material as the microneedles. Additionally or alternatively, the backing member may be formed from any other material suitable for such purposes. In some embodiments, the backing member is flexible. In some embodiments, the backing member is in the form of a solid sheet or platform, such as a sheet (e.g., layer) comprising a suitable material, such as PVP, polyvinylalchol, pullulan, chitosan, gelatin, sodium alginate, cellulose, polyacrylamide, poly(N-isopropylacrylamide) or its copolymers, hydroxypropylcellulose, hydroxypropylmethylcellulose, hydroxyethylcellulose, carboxymethylcellulose, silk polymer, amylopectin, chondroitin sulfate, poly(lactic-co-glycolic acid), fibrin, elastin, collagen, hyaluronic acid, dextran, functionalized or modified species of the above, or mixtures or blends of two or more of the above. In other embodiments the backing member is in the form of a membrane, such as a flexible mesh membrane comprised of any suitable material, such as a flexible mesh membrane comprising nylon, polypropylene, stainless steel, ethylene-vinyl acetate, polyethylene terephthalate, polyurethane, woven or non-woven fabric, or combinations, mixtures or blends of two or more thereof.

In embodiments where the backing member is not integrally formed with the microneedles, the microneedle array may be applied to the backing member by any means known in the art, such as by using an adhesive material to adhere the microneedle array to the backing member or by heat-sealing the microneedle array to the backing member In accordance with any of the embodiments of microneedles and backing members described herein, the array of microneedles may be disposed on the backing member such that there is a peripheral border region on the backing member that does not comprise microneedles. The border may extend along the entire circumference of the backing member, or may be only on one or more portions thereof, such as one or more sides (or portions thereof) of a polygon-shaped backing member or one or more arcs of a round (e.g., circular or oval) backing member.

In specific embodiments, at least a portion of a border is provided with an adhesive to adhere the microneedle device to the skin surface during use. The adhesive may comprise any adhesive suitable for such use. In specific embodiments, the adhesive is a pressure-sensitive adhesive. In some embodiments, the entire border is provided with an adhesive. In other embodiments, only a portion of the border is provided with an adhesive. As used herein, the term "pressure-sensitive adhesive" refers to a viscoelastic material which adheres instantaneously to most substrates with the application of very slight pressure and remains tacky. A polymer is a pressure-sensitive adhesive within the meaning of the term as used herein if it has the properties of a pressure-sensitive adhesive per se or functions as a pressure-sensitive adhesive by admixture with tackifiers, plasticizers or other additives.

In any embodiments with an adhesive, the microneedle device may further comprise a removable release layer over the adhesive. When present, the release liner is removed from the device prior to use to expose the adhesive prior to application of the device. Materials suitable for use as release liners are well-known known in the art.

Figure 2A:
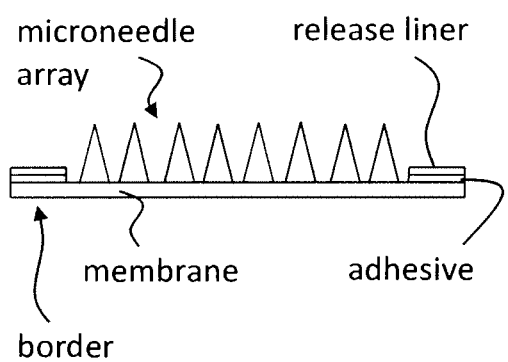
FIG. 2A is a side view of a microneedle device according to a second embodiment described herein.
Figure 2B:
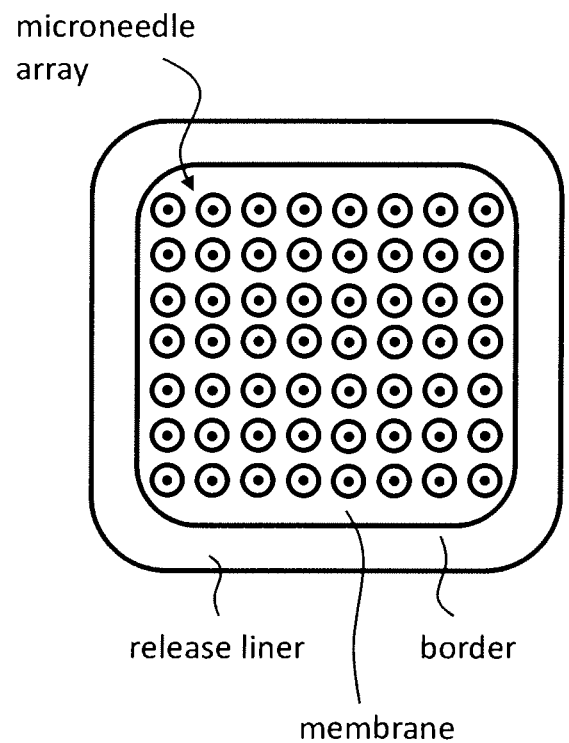
FIG. 2B is a top view of the microneedle device depicted in FIG. 2A.

Turning to the figures, FIG. 1 is a front, top perspective view of a microneedle device according to a first embodiment of the invention. The microneedle device includes an array of a plurality of microneedles disposed on a backing member (also referred to as a "basement"). As depicted in FIG. 1, the backing member could be formed integrally with the microneedle array or could be made of a different material, such as a material that is more flexible than the microneedle array. In another embodiment, shown in FIGS. 2A and 2B, the backing member is in the form of a flexible membrane, such as a flexible mesh membrane, such as a membrane made of, for example, nylon, polypropylene, or stainless steel. In the embodiments shown in FIGS. 1, 2A, and 2B, the backing member of the microneedle device includes a border extending peripherally around the microneedle array. As noted above and illustrated in FIGS. 2A and 2B, in some embodiments the border is provided with an adhesive to adhere the microneedle device to the skin surface during use, and a release liner covering the adhesive prior to use. The adhesive and release liner may be applied before or after irradiation of the microneedles.

The microneedle array may include from tens to several hundred microneedle projections per square centimeter. For example, the microneedle array may include 10 or more microneedles, 100 or more, or 1000 or more microneedles, including from about 50 to about 1000 per square centimeter, such as 200, 400, 500 or 900 microneedles per square centimeter. The dimensions of the microneedle can be selected and adjusted depending on the intended use (e.g., drug delivery or sampling). Typically, microneedles have a cone or square pyramid shape. Typically, microneedles have a length of from about 100 to about 1000 µm, including a length of about 200, 400 or 600 µm. Typically, microneedles have a base diameter of from about 100 to about 00 µm, including a base diameter of from about 120 to about 300 µm, such as a base diameter of about 120 µm or about 300 µm. A typical tip angle may be, for example, in a range of 10° to 45°, for example 34°. The needle-to-needle spacing per square centimeter can be selected and adjusted depending on the intended use (e.g., drug delivery or sampling, and specific drug(s) being delivered or material(s) being sampled). Typically, a microneedle array may have a needle-to-needle spacing per square centimeter of from about 50 to about 1000 µm, including from about 200 µm to about 400 µm. The spacing may be uniform or varied across the surface of the array. Typically, a microneedle may have an aspect ratio (ratio of microneedle length to base diameter) of from 0.5 to 3, including an aspect ratio of about 1.67. A typical device may have a needle density of 30%.

In accordance with any of the embodiments described herein, the microneedle device may be free of, or substantially free of, chemical and physical crosslinking agents, such as being free of, or substantially free of, any one or more or all of the following: peroxides, vinylsilanes, triethanolamine, bisacrylamide, polycarboxylic acids, halogenated dicarboxylic acids, polycarboxylic anhydrides, aldehyde compounds, N-methylol compounds, metaphosphoric acid salts, divinyl compounds, bis-aziridine, ethylene-vinyl acetate, isocyanate compounds, aluminum hydroxide, silanol compounds, epoxy compounds, melamine compounds, carbodimide compounds, hydrazide compounds, ester compounds, and epichlorohydrin, or the like.

Drug-Containing Microneedle Devices

For drug delivery, one or more drugs may be incorporated in the polymer material of the microneedles, or may be provided separately. When the drug is incorporated in the polymer material of the microneedles, it may be formulated in the solution of polymer material that is used to form the intermediate microneedle array structure, as discussed in more detail below. When the drug is provided separately, it may be provided in a component, composition, coating, or layer provided on one or more of an exterior or interior surface of the microneedles and/or on at least one face of the device (e.g., the "front" face from which the microneedles protrude into the skin and/or the opposite "back" face), such as any composition described in more detail below. In some embodiments, the drug is applied to the microneedle device during the manufacturing process, such that the final product is a drug-containing microneedle device. In other embodiments, the drug is applied to the device at the time of use. In accordance with the latter embodiments, the microneedle device and drug-containing component or composition may be provided in separate packages (optionally packaged together) with instructions to apply the drug-containing component or composition to the microneedle device prior to use. In some embodiments, the drug may be provided in a separate drug delivery device, such as an iontophoresis device, a sonophoresis device, a magnetphoresis device, etc. In accordance with those embodiments, the microneedle device may be employed prior to the drug delivery device, or they may be used together, such as by applying or attaching the drug delivery device to the microneedle device. In some embodiments, a drug may be both incorporated in the polymer material of the microneedles and provided separately, such as applied to one or more of an exterior or interior surface of the microneedles and/or on a face of the device, and/or as a separate component. In such embodiments, the same or different drug(s) may be used in the microneedle polymer material and elsewhere, and the drug(s) may be formulated in the same or different compositions, in the same or different form, and any permutation or combination thereof.

In specific embodiments, the drug is provided in a flexible, finite transdermal drug delivery system (e.g., in a transdermal drug delivery patch) disposed on a face of the device, such as patch disposed on the back face of the device, such as on the back face of the backing member. In accordance with some embodiments, the microneedle device is configured to support the patch, such as by having dimensions suitable for supporting the patch. In some embodiments, the microneedle device and patch may be provided in separate packages (optionally packaged together) with instructions to remove the release liner from the patch and apply it to the back face of the microneedle device.

In other specific embodiments, the drug is provided in a drug-containing composition (e.g., in a transdermal drug delivery composition) that is provided on one or more of an exterior or interior surface of the microneedles and/or on applied to a face of the device, such as composition applied to the back face of the device, such as on the back face of the backing member. In some embodiments, the composition is a solid (including powder), semi-solid, liquid, gel, ointment, cream, emulsion, or polymeric composition that is applied to one or more of an exterior or interior surface of the microneedles and/or on at least one face of the backing member. In any of these embodiments, the drug may be formulated in any suitable form, including being dissolved, dispersed or suspended in a composition. In embodiments where the drug is in solid form, the drug may be in any solid form, including any crystalline or amorphous form, and/or provided as a particles (e.g., drug-encapsulated particles, coated drug particle, drug nanoparticles, etc.). In some embodiments where a drug-containing composition is applied to a back face of the device, the composition may be provided with a covering material that, together with the microneedle device, defines a cavity that contains the drug-containing composition In such embodiments, the covering material and drug-containing composition together may be referred to as a "patch" although the "patch" may be formed at the time of use. See, e.g., FIG. 3. In accordance with any of these embodiments, the microneedle device and drug-containing composition may be provided in separate packages (optionally packaged together) with instructions to apply the composition to the microneedle device and, optionally, cover it with a covering material. In some embodiments, the drug-containing composition is provided in a unit dose package (such as a packet or pre-filled syringe) or in a unit dose pump.

Figure 3:
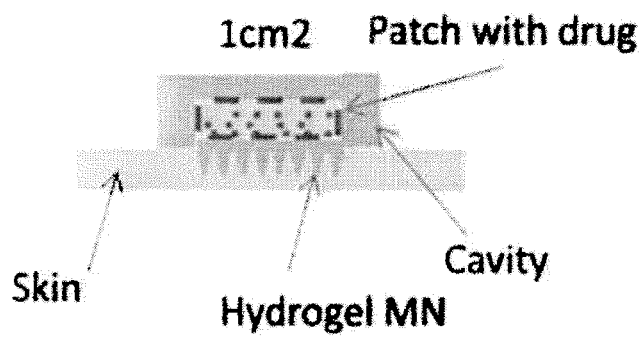
FIG. 3 is a side, cross-sectional view of a microneedle device according to a third embodiment described herein, shown after placement in the skin of a patient.

Turning again to the figures, FIG. 3 illustrates a microneedle device that includes a patch-type transdermal drug delivery system disposed on the back face of the device. As shown in the figure and discussed above, the patch may include a cavity that holds a drug-containing composition, such as a semi-solid, liquid, gel, ointment or emulsion formulation of the drug.

In use, the microneedles pierce the skin, facilitating transdermal drug delivery from the device into the skin.

As noted above, the microneedle devices can be prepared such that they have a tendency to dissolve or swell, which impacts drug delivery. The properties of the drug-containing composition (e.g., the nature of the composition, the concentration of drug, the presence of enhancers, etc.) also will impact drug delivery. Still further, drug-containing compositions that include one or more component(s) that interact(s) with the microneedles, such as water or another solvent or other component, may impact drug delivery, such as by impacting physical or physicochemical properties of the microneedles, such as by promoting dissolution and/or swelling of the microneedles. Additionally or alternatively, drug-containing compositions may include one or more component(s) that interact(s) with the material of the microneedle backing member, such as water or another solvent or other component, that may impact the physical properties of the device. For example, compositions may be formulated so as not to promote swelling of the devices during storage, such as by using pH-sensitive hydrogels that are resistant to swelling due to humidity, temperature-responsive hydrogels that respond to physiological temperature, or bio-responsive hydrogels that respond to a molecule present in the skin, such as an enzyme or other protein, glucose or other carbohydrate, etc.

Manufacturing Methods

As noted above, methods of manufacturing the microneedle devices described herein generally include a first step of forming an intermediate microneedle array structure and a second step of treating the intermediate microneedle array structure with electron beam or photo-irradiation (such as ultraviolet, infrared, or microwave irradiation) to crosslink the polymer material and, optionally, sterilize the device. These two steps can be accomplished by various means known separately in the art.

In some embodiments, the intermediate microneedle array structure is formed by a mold process. For example, a solution comprising electron beam crosslinkable or photocrosslinkable polymer material is coated or cast into a mold that comprises a plurality of microneedle-shaped recesses to form an intermediate microneedle array structure. A squeegee or centrifuge may be used to fill the mold. In other embodiments, the intermediate microneedle array structure is formed by a casting process. For example, a solution comprising electron beam crosslinkable or photocrosslinkable polymer material is cast into a sheet (typically having a thickness of several millimeters) which is then hot-embossed with an embossing member to form an intermediate microneedle array structure. In other embodiments, the intermediate microneedle array structure is formed by an extrusion process. For example, a solution comprising electron beam crosslinkable or photocrosslinkable polymer material is extruded to form a sheet (typically having a thickness of several millimeters) which is then hot-embossed with an embossing member to form an intermediate microneedle array structure. In other embodiments, the intermediate microneedle array structure is formed using 3D printing technology.

In accordance with any of these embodiments, the solution comprising electron beam crosslinkable or photocrosslinkable polymer material may comprise, for example, 0.1-75% w/v of the polymer material in water or evaporable solvent.

In accordance with any of these embodiments, the microneedle array structure may be subject to a drying step before or after the irradiation step described below.

In accordance with any of these embodiments, the microneedle array structure may be applied to a backing member before or after the irradiation step described below.

After the intermediate microneedle array structure is formed, it is irradiated with electron beam or photo-irradiation, such as ultraviolet, infrared, or microwave radiation, to induce crosslinking of the polymer material, e.g., to induce crosslinking between polymer chains of the polymer material, and thereby produce microneedles as described herein. Typically, the absorbed radiation dose may be between about 10 and about 600 kilograys, including from about 10 to about 300 kilograys In some embodiments, the irradiation sterilizes the microneedles. This is in contrast to microneedle devices made using chemical crosslinking processes, which require a separate sterilization step. A radiation dose of at least about 15 kilograys, or about 25 kilograys, generally is sufficient for sterilization.

As discussed above, and illustrated in the examples below, the extent of polymer crosslinking can be readily and consistently selected and controlled by selecting and controlling the radiation dose, which in turn allows for the selection and control of whether the device dissolves (generally at lower radiation doses/less crosslinking) or swells (generally at higher radiation doses/more crosslinking). The extent of crosslinking also impacts the strength and hardness of the microneedles. Further, as discussed in more detail below, the extent of crosslinking and dissolvability vs. swellability also impact drug delivery, e.g., the rate at which drug diffuses from the device. Thus, by selecting and controlling the electron bean or photo-irradiation and extent of crosslinking, microneedle devices can be prepared that provide sustained drug delivery over an extended period of time.

As discussed above, in embodiments where the microneedle device can be used for drug delivery, one or more drugs may be incorporated in the polymer material of the microneedles, or may be provided separately. When the drug is incorporated in the polymer material, it may be provided in the solution that comprises the polymer material. In other embodiments, the drug may be provided in a component, composition, coating or layer on one or more of an exterior or interior surface of the microneedles and/or on at least one face of the device, such as being formulated in a composition as discussed above, that is applied to one or more of an exterior or interior surface of the microneedles and/or at least one face of the backing member. For example, in some embodiments, one or more drugs is formulated in a composition that is coated onto an exterior surface of the microneedles, coated onto an interior surface of the microneedles (or otherwise provided inside the microneedles), or applied to at least one face of a backing member of the device. In accordance with any of these embodiments, the device may be dried before further processing.

As discussed above, in some embodiments, the drug is provided in a flexible, finite transdermal drug delivery system (e.g., in a transdermal drug delivery patch) that is applied to or disposed on a face of the device, such as patch that is applied to or disposed on the back face of the backing member. Any transdermal drug delivery system may be used in accordance with these embodiments. In some embodiments, the dimensions of the microneedle device are configured to support the transdermal drug delivery system. In some embodiments, the transdermal drug delivery system is prepared and/or packaged separately from the microneedle device and applied to the microneedle device by the user just prior to use. In other embodiments, the transdermal drug delivery system is packaged together with the microneedle device.

The finished microneedle device may be packaged in a humidity controlled package material, such as a laminated pouch.

Transdermal Drug Delivery Methods

As noted above, the microneedle devices described herein can be used, for example, for transdermal drug delivery or for sampling biological fluids from a subject. For either use, the microneedle devices described herein are applied to the skin surface of the subject. In some embodiments, light pressure is applied to facilitate the microneedles' piercing of the skin. As noted above, if the device includes a release liner, it is removed prior to use.

In a dry state, such as just prior to use, the microneedles described herein have sufficient strength to pierce the stratum corneum. When inserted into the skin, the polymer material of the microneedles absorbs moisture (e.g., water) from the skin. Depending on the processing conditions used to make the microneedles (e.g., depending on the dose of electron beam or photo-irradiation and/or extent of crosslinking), this absorption of water may cause the microneedles to slowly dissolve or swell. In general, dissolving microneedles yield faster drug delivery, while swellable microneedles yield sustained delivery.

In embodiments where the devices are used for transdermal drug delivery, the manufacturing process can be selected and controlled to select and control drug delivery from the device, such as by selecting and controlling the extent of crosslinking to provide sustained drug delivery. For example, the polymer material can be electron beam crosslinked or photocrosslinked to such an extent that the microneedle device is adapted to provide drug delivery over an extended period of time, such as ranging from a few minutes, up to an hour, a few hours, or longer, including providing drug delivery over at least 1 hour, at least 2 hours, at least 3 hours, at least 4 hours, at least 6 hours, at least 8 hours, at least 12 hours, at least 24 hours, at least 30 hours, at least 36 hours, at least 72 hours, or longer. Depending on the drug and how it is formulated, such an extended period of drug delivery can result in desired pharmacokinetic profiles, such as relatively constant plasma levels of drug, gradually increasing plasma levels of drug, etc.

EXAMPLES

Example 1

Microneedle Devices

A solution of electron beam crosslinkable polymer material is made by preparing a polyvinylpyrrolidone (PVP)/ water solution at 250 mg of PVP/ml of water, using Kollidon K-90 as the PVP. A silicon mold is used, having conical holes with a depth of 500 μm, a density of 400 holes/cm², and a base diameter of 300 μm. After mixing to a clear solution, the solution and mold are centrifuged at 5000 rpm for 15 minutes. The solution is fried under ambient conditions for three hours. After drying, additional solution is added to the mold to form a backing member (also referred to as a "basement"). The polymer-filled mold is dried overnight at room temperature, after which the formed intermediate microneedle array structures are removed and packaged and stored in a controlled humidity environment until electron beam irradiation.

In some embodiments, the backing member is formed by adding additional solution to the mold and covering with a nylon mesh, for example. This results in a more flexible device.

Dry intermediate microneedle array structures are irradiated with electron beam irradiation, such as by placing them in an electron beam accelerator (Electron Technologies Corp, CT) to achieve an absorbed radiation dose in the range of from about 10 to about 300 kilograys.

Adhesive layers and release liners are attached around the microneedles.

The microneedles have a height of about 500 μm, and a tip angle of about 34°. The needle density is about 400 needles/cm². The effective area covered by the microneedles is about 30% (0.3 cm² out of 1.0 cm² of microneedle array area). The total area of skin treated with microneedles is about 0.045 cm² per cm² of apparent total microneedle array area, with an insertion depth of 200 μm.

Electron beam crosslinked microneedle devices prepared as described above were subjected to penetration testing by inserting the microneedle devices into cadaver skin with thumb pressure for about 30 seconds and then removing them. Treated skin sites were dyed with methylene blue to image penetration. It was expected that electron beam irradiation would make the PVP fragile, causing breakage upon insertion into the skin. However, surprisingly, the results showed that 100% of the microneedles penetrated into the skin without breakage.

Example 2

Effect of Irradiation on Microneedle Properties

When microneedles are manufactured as described above using a water-soluble PVP without electron beam crosslinking, tips of the microneedles (about 200 μm in length) dissolve within one hour of insertion into skin. Treating the microneedles with electron beam irradiation diminishes this dissolution property, and promotes swellability of the microneedles.

Microneedle devices were manufactured using varying radiation doses in the range of 10 to 300 kilograys, exposed to water and then monitored for dissolution and/or swelling. At the low end of the radiation dose range, the microneedles slowly dissolved in water, with the dissolution time increasing with radiation dose. At the high end of the radiation dose range, the microneedles became swollen with water. Results are summarized in Table 1.

TABLE 1

| E-beam Dose | 0 kGy | 10 kGy | 50 kGy | 100 kGy | 200 kGy | 300 kGy |
| --- | --- | --- | --- | --- | --- | --- |
| MNs property | dissolvable | slowly dissolvable | slowly dissolvable | swellable | swellable | swellable |

Example 3

In Vitro Drug Delivery

A methylphenidate gel composition is prepared by dissolving 8.0 g methylphenidate hydrochloride into 38 g glycerol. After complete dissolution, 0.4 g aluminum hydroxide gel and 5.0 g N-vinylacetamide/sodium acrylate copolymer (GE-167) is added. A citric acid solution is made by adding 0.4 g of citric acid into 48.2 g of deionized water. The citric acid solution is gradually added to the methylphenidate mixture to form the methylphenidate gel composition.

Figure 4A:
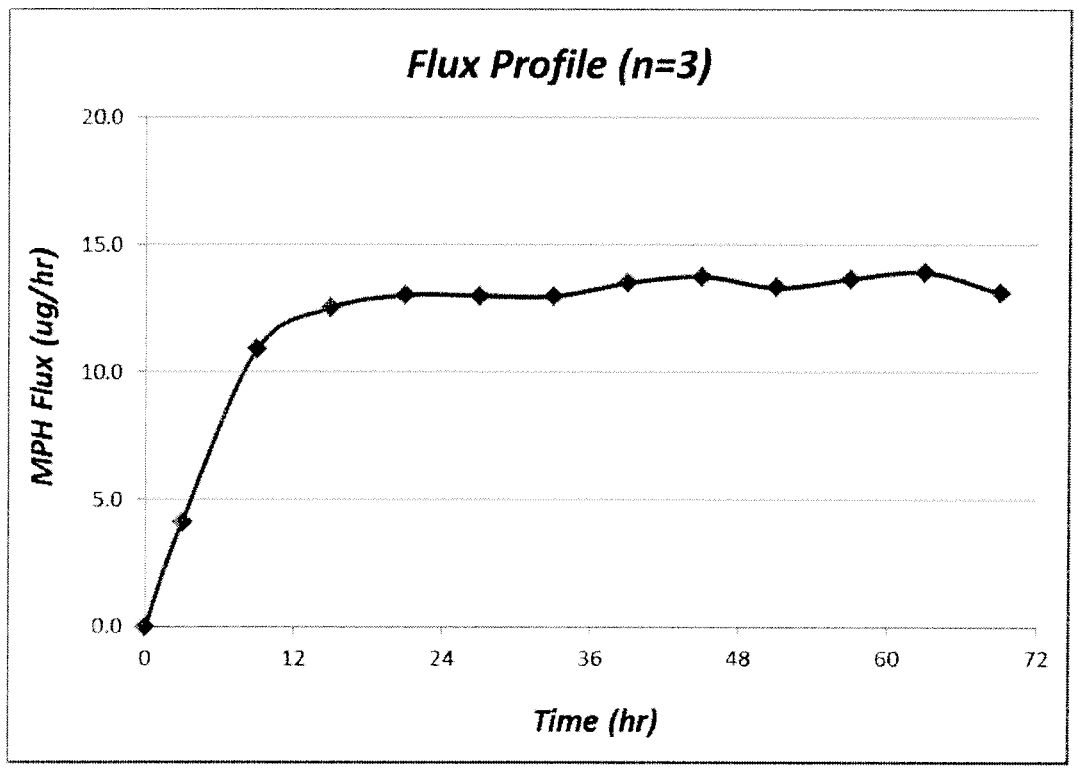
FIG. 4A illustrates the in vitro drug flux through the skin of methylphenidate through a microneedle device as described herein, when tested using a modified Franz-diffusion type cell set-up.

A methylphenidate gel composition prepared as described above is applied to the back face of a microneedle device prepared as described in Example 1 (using an absorbed radiation dose of 300 kGy) at an amount of 1 g/cm² (70 mg/cm², based on the amount of methylphenidate free base), and provided with a covering layer of closed cell polyolefin foam tape (3M. St. Paul, Minn.). Drug delivery through human cadaver skin was assessed using a modified Franz-diffusion type cell. The Franz cell receiver compartment was periodically assayed for methylphenidate. Results are shown in FIG. 4A. As shown in the figure, the device achieved sustained delivery of methylphenidate over the 72 hour test period, with a sustained drug flux.

Figure 4B:
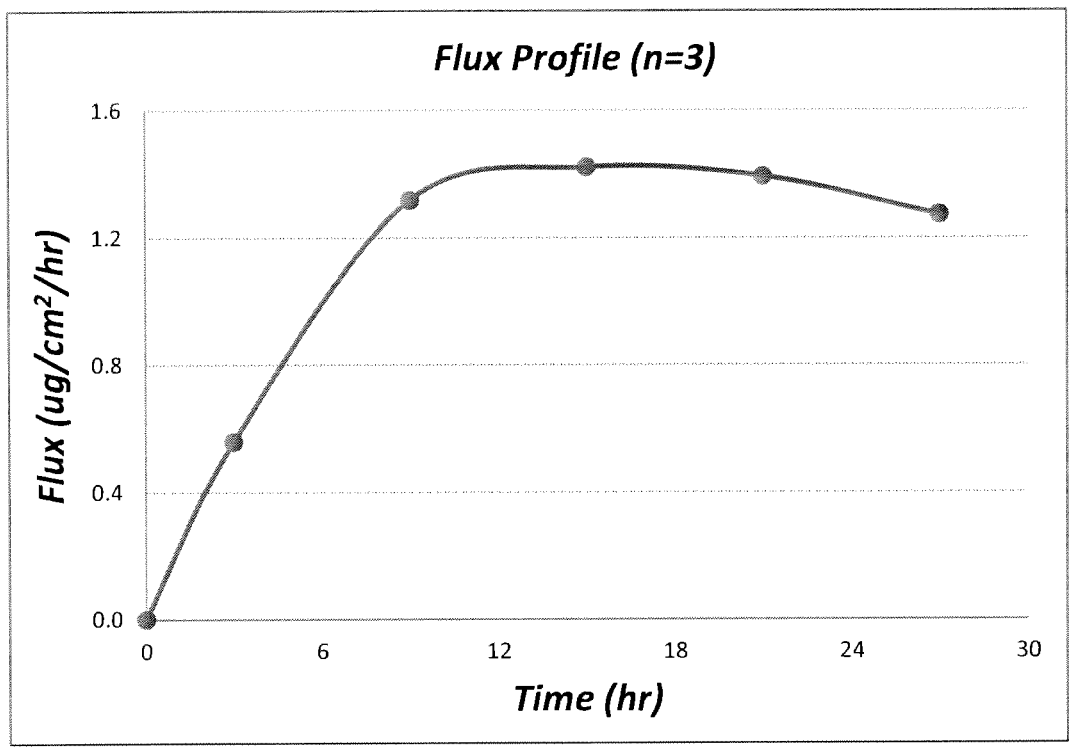
FIG. 4B illustrates the in vitro drug flux through the skin of sodium diclofenac through a microneedle device as described herein, when tested using a modified Franz-diffusion type cell set-up.

A microneedle device prepared as described in Example 1 using an absorbed radiation dose of 300 kGy was inserted into human cadaver skin and a transdermal drug delivery patch comprising sodium diclofenac was applied to the back face of the microneedle device. Drug delivery through human cadaver skin was assessed using a modified Franz-diffusion type cell. The Franz cell receiver compartment was assayed periodically for sodium diclofenac. Results are shown in FIG. 4B. As seen in the figure, significant, sustained drug delivery through the microneedle device and skin was achieved over a period of time of at least 24 hours.

Example 4

In Vivo Drug Delivery

Drug delivery through microneedle devices prepared as described in Example 1 was assessed in vivo in swine.

Figure 4C:
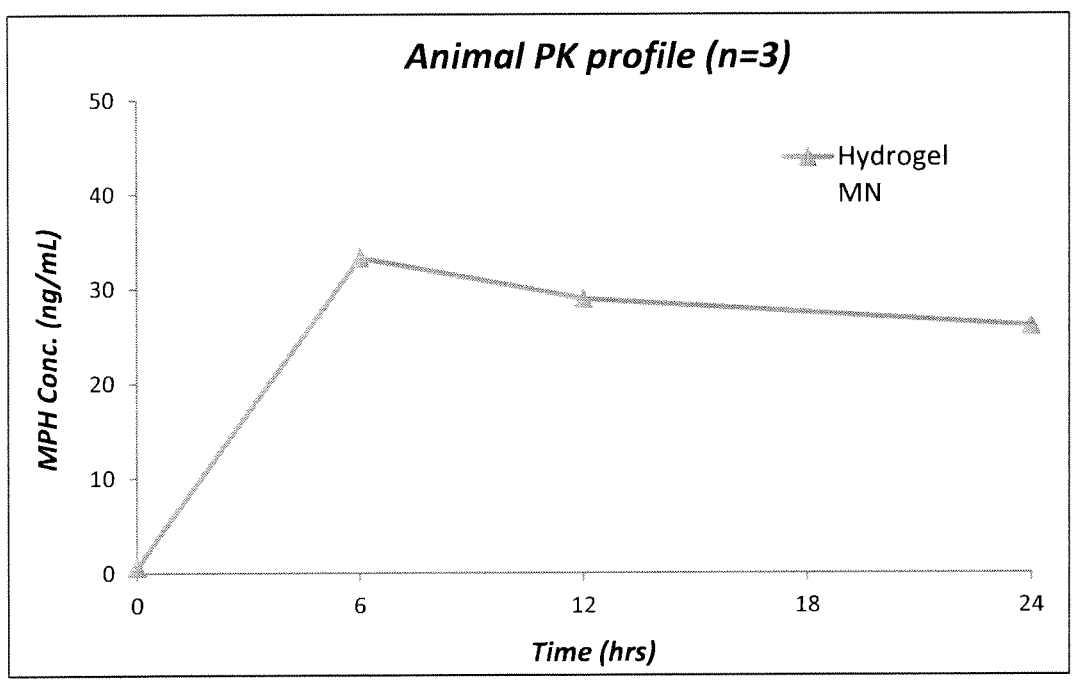
FIG. 4C illustrates the pharmacokinetics (plasma concentration) of methylphenidate through a microneedle device as described herein, when tested in vivo in swine.

A methylphenidate gel composition prepared as described above was applied to the back face of a microneedle device prepared as described in Example 1 (using an absorbed radiation dose of 300 kGy) at an amount of 1 g/cm² (70 mg/cm², based on the amount of methylphenidate free base), and provided with a covering layer of closed cell polyolefin foam tape (3M. St. Paul, Minn.). Blood samples were taken periodically and assayed for methylphenidate. Results are shown in FIG. 4C. As seen in the figure, plasma methylphenidate concentration increased to over 30 ng/mL in six hours and was sustained at a substantially constant level (i.e., varying by 30% or less) for 24 hours.

A similar experiment was performed using a rivastigmine gel composition or a rivastigmine water-based composition, using a microneedle device prepared as described in Example 1 (subject to an absorbed radiation dose of 300 kGy), using nylon mesh to form the backing member.

A rivastigmine gel-based composition is prepared by dissolving 3.4 g rivastigmine tartrate into 84 g dispersed particle gel, followed by adding 12.6 g of hydroxypropyl cellulose gel. A rivastigmine water-based composition is prepared by dissolving 3.4 g rivastigmine tartrate into 37 g water and 7 g 1N NaOH solution, followed by adding 32.6 g hydroxypropyl cellulose gel.

The microneedle devices are inserted into the skin of a swine by hand and then a closed-cell polyolefin foam tape is used to make a cavity for holding the rivastigmine compositions that are applied to the back face of the microneedle devices. Every animal was treated with two devices on both flank sides, for a total of eight microneedle treatments per animal (covering a total area of 2×4 cm$^2$). Blood samples were taken periodically and assayed for rivastigmine.

Figure 4D:
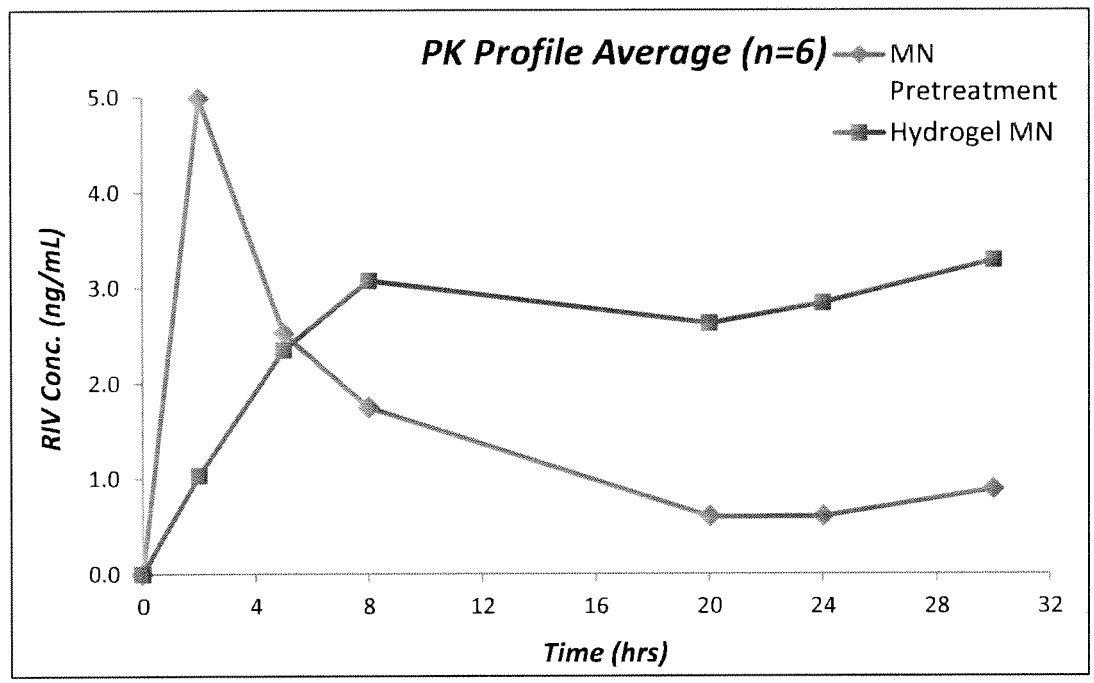
FIG. 4D illustrates the pharmacokinetics (plasma concentration) of rivastigmine (i) through a microneedle device using a gel-based composition as described herein and (ii) using a gel-based composition after pretreatment with a prior art microneedle device, when tested in vivo in swine.

FIG. 4D. shows results for the rivastigmine gel-based composition along with results achieved using microneedle pretreatment with a microneedle device that is not made of electron beam crosslinked polymer material. In microneedle pretreatment, a microneedle device is used to pierce the skin and is removed before the drug-containing composition is applied to the skin. The microneedle devices used for pretreatment were made of poly-L-lactide and shaped as square pyramids with a height of about 500 µm, a tip angle of about 20°, and a needle density of about 640 needles/cm$^2$. The effective area covered by the microneedles was about 20% (0.2 cm$^2$ out of 1.0 cm$^2$ of microneedle array area). The total area of skin pretreated with microneedles was about 0.03 cm$^2$ per cm$^2$ of apparent total microneedle array area, with an insertion depth of 200 µm. A spring-powered applicator delivering an energy of approximately 0.4 J/cm$^2$ is used for applying the pretreatment microneedles to the skin.

As seen in FIG. 4D, the microneedle device as described herein with the rivastigmine gel-based composition achieved a drug delivery that resulted in a plasma rivastigmine concentrations that increased to about 3 ng/mL in eight hours and was sustained at a substantially constant level (i.e., varying by 30% or less) for 30 hours. In contrast, pretreatment with a conventional microneedle device followed by application of a rivastigmine gel-based composition resulted in plasma rivastigmine concentrations that peaked at about 5 ng/mL at two hours and then dropped about 50% to about 2.5 ng/mL at four hours, and fell to less than 1 ng/mL by 20 hours.

Figure 4E:
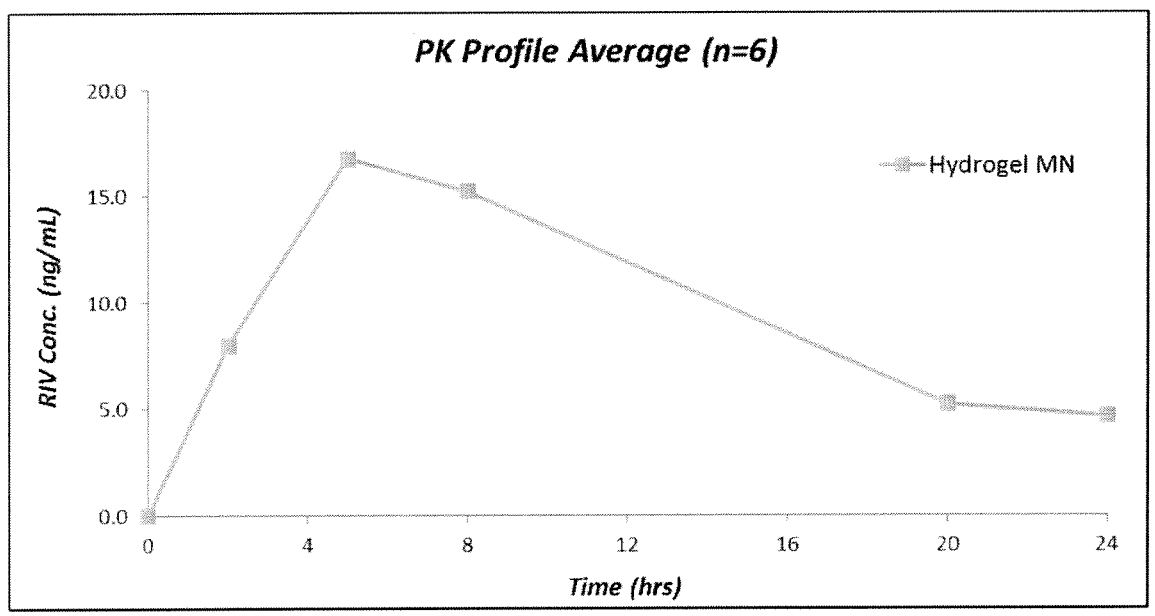
FIG. 4E illustrates the pharmacokinetics (plasma concentration) of rivastigmine through a microneedle device as described herein using a water-based composition as described herein.

FIG. 4E. shows results for the rivastigmine water-based composition. As seen in the figure, this composition achieved a drug delivery that resulted in a plasma rivastigmine concentrations that peaked at about 17 ng/mL at about 5 hours and then declined at a relatively constant rate over about 15 hours. While not wanting to be bound by theory, it is believed that the water-based formulation promoted dissolution of the microneedles, resulting in faster drug delivery.

These results show that the microneedle devices described herein can be designed to achieve different drug delivery and pharmacokinetic profiles, such as sustained drug delivery and relatively constant plasma levels over an extended period of time, or more rapid drug delivery and relatively rapid attainment of high drug plasma concentrations.

The foregoing description is provided for purposes of illustration and description, and is not intended to be exhaustive or to limit the invention. The invention includes all possible permutations and combinations of specific features of the embodiments described herein.

What is claimed is:

1. A microneedle device comprising an array of a plurality of microneedles, wherein
   the microneedles are formed of an electron beam crosslinked or photocrosslinked polymer material, wherein a drug is incorporated in the electron beam crosslinked or photocrosslinked polymer material, and
   an exterior or interior surface of the microneedles and/or a face of the device has a separate drug-containing composition applied thereon, separate from and in addition to the drug incorporated in the microneedle polymer material.

2. The device of claim 1, wherein the electron beam crosslinked or photocrosslinked polymer material is a hydrogel material.

3. The device of claim 1, wherein the electron beam crosslinked or photocrosslinked polymer material comprises one or more materials selected from the group consisting of polyvinylpyrrolidone (PVP), polyethylene oxide, polyvinylalchol, polyacrylamide, poly(N-isopropylacrylamide) or its copolymers, dextran, pullulan, chitosan, gelatin, sodium alginate, cellulose, hydroxypropylcellulose, hydroxypropylmethylcellulose, hydroxyethylcellulose, carboxymethylcellulose, silk polymer, amylopectin, chondroitin sulfate, poly (lactic-co-glycolic acid), fibrin, elastin, collagen, hyaluronic acid, functionalized or modified above polymers, and mixtures and blends of two or more thereof.

4. The device of claim 3, wherein the electron beam crosslinked or photocrosslinked polymer material comprises PVP.

5. The device of claim 3, wherein the electron beam crosslinked or photocrosslinked polymer material further comprises a plasticizer.

6. The device of claim 5, wherein the plasticizer comprises one or more plasticizers selected from the group consisting of polyethyleneglycol, liquid paraffin, dioctyl phthalate, diisononyl phthalate, diisodecyl phthalate, dibutyl phthalate, dioctyl adipate, diisononyl adipate, trioctyl trimellitate, tricresyl phosphate, acetyl tributyl citrate, epoxidized soybean-oil, epoxidized linseed-oil, sebacate.

7. The device of claim 1, wherein the array is disposed on a backing member.

8. The device of claim 7, wherein the backing member is in the form of a sheet comprising one or more materials selected from the group consisting of PVP, polyvinylalchol, pullulan, chitosan, gelatin, sodium alginate, cellulose, polyacrylamide, poly(N-isopropylacrylamide) or its copolymers, hydroxypropylcellulose, hydroxypropylmethylcellulose, hydroxyethylcellulose, carboxymethylcellulose, silk polymer, amylopectin, chondroitin sulfate, poly(lactic-co-glycolic acid), fibrin, elastin, collagen, hyaluronic acid, dextran, functionalized or modified above polymers, and mixtures or blends of two or more thereof.

9. The device of claim 7, wherein the backing member is in the form of a flexible mesh membrane comprising one or more materials selected from the group consisting of nylon, polypropylene, stainless steel, ethylene-vinyl acetate, polyethylene terephthalate, polyurethane, woven or non-woven fabric.

10. The device of claim 7, wherein the array is disposed on the backing member such that the backing member comprises a peripheral border region that does not comprise microneedles.

11. The device of claim 10, wherein at least a portion of the peripheral border region is provided with an adhesive.

12. The device of claim 11, further comprising a release liner overlaying the adhesive.

13. The device of claim 1, wherein the array comprises from 50 to 1000 microneedles per square centimeter.

14. The device of claim 1, wherein an average height of the microneedles is from 100 to 1000 µm.

15. The device of claim 1, wherein the microneedles dissolve in water.

16. The device of claim 1, wherein the microneedles swell in water.

17. The device of claim 1, wherein the drug included in the electron beam crosslinked or photocrosslinked polymer material is different from the drug in the drug-containing composition.

18. The device of claim 1, having a front face from which the microneedles protrude and a back face opposite the front face, wherein the drug-containing composition is provided as a flexible, finite transdermal drug delivery system or a drug-containing semi-solid, liquid, gel, ointment or emulsion composition disposed on the back face.

19. The device of claim 1, wherein the device provides sustained delivery of the drug over a period of time selected from the group consisting of at least 1 hour, at least 2 hours, at least 3 hours, at least 4 hours, at least 6 hours, at least 8 hours, at least 12 hours, at least 24 hours, at least 30 hours, at least 36 hours, and at least 72 hours.

20. A method of making a microneedle device comprising an array of a plurality of microneedles, the method comprising:
    forming an intermediate microneedle array structure from a solution comprising an electron beam crosslinkable or photocrosslinkable polymer material and a drug, and irradiating the intermediate microneedle array structure with electron beam, ultraviolet, infrared, or microwave radiation to induce crosslinking of the electron beam crosslinkable or photocrosslinkable polymer material, thereby forming microneedles formed of an electron beam crosslinked or photocrosslinked polymer material, wherein a drug is incorporated in the electron beam crosslinked or photocrosslinked polymer material, and
    applying a separate drug-containing composition onto an exterior or interior surface of the microneedles and/or a face of the device so as to provide the separate drug-containing composition separately from and in addition to the drug incorporated into the microneedle polymer material.

21. The method of claim 20, wherein the electron beam crosslinkable or photocrosslinkable polymer material comprises one or more materials selected from the group consisting of polyvinylpyrrolidone (PVP), polyethylene oxide, polyvinylalchol, polyacrylamide, poly(N-isopropylacrylamide) or its copolymers, dextran, pullulan, chitosan, gelatin, sodium alginate, cellulose, hydroxypropylcellulose, hydroxypropylmethylcellulose, hydroxyethylcellulose, carboxymethylcellulose, silk polymer, amylopectin, chondroitin sulfate, poly(lactic-co-glycolic acid), fibrin, elastin, collagen, hyaluronic acid, functionalized or modified above polymers, and mixtures and blends of two or more thereof.

22. The method of claim 21, wherein the electron beam crosslinkable or photocrosslinkable polymer material comprises PVP.

23. The method of claim 21, wherein the electron beam crosslinkable or photocrosslinkable polymer material further comprises a plasticizer.

24. The method of claim 20, wherein the intermediate microneedle array structure is formed by a process selected from the group consisting of coating the solution into a mold, casting the solution in a mold, casting the solution into a sheet followed by embossing, extruding the solution into a sheet followed by embossing, and 3D printing.

25. The method of claim 20, further comprising a drying step before or after the irradiating step.

26. The method of claim 20, further comprising, before or after the irradiating step, applying the microneedle array structure to a backing member.

27. The method of claim 20, wherein the irradiating step provides an absorbed radiation dose of from 10 to 600 kilograys.

28. The method of claim 20, wherein the irradiating step provides an absorbed radiation dose of at least 100 kilograys.

29. The method of claim 20, wherein the irradiating step provides an absorbed radiation dose of about 300 kilograys.

30. The method of claim 20, wherein the device has a front face from which the microneedles protrude and a back face opposite the front face, wherein the drug-containing composition is applied as a flexible, finite transdermal drug delivery system or a semi-solid, liquid, gel, ointment or emulsion drug-containing composition to the back face.

31. A microneedle device made by a method as claimed in claim 20.

32. A method of delivering a drug to a subject in need thereof, comprising applying a microneedle device as claimed in claim 1 to the skin of the subject.

33. A method of sampling a biological fluid from a subject, comprising applying a microneedle device as claimed in claim 1 to the skin of the subject.

34. A method of delivering a drug to a subject in need thereof, comprising applying a microneedle device as claimed in claim 1 to the skin of the subject.

35. A method of delivering a drug to a subject in need thereof, comprising applying a microneedle device as claimed in claim 18 to the skin of the subject.

36. The device of claim 1, wherein the device provides sustained delivery of the drug over a period of time selected from the group consisting of at least 1 hour, at least 2 hours, at least 3 hours, at least 4 hours, at least 6 hours, at least 8 hours, at least 12 hours, at least 24 hours, at least 30 hours, at least 36 hours, and at least 72 hours.

37. The device of claim 18, wherein the device provides sustained delivery of the drug over a period of time selected from the group consisting of at least 1 hour, at least 2 hours, at least 3 hours, at least 4 hours, at least 6 hours, at least 8 hours, at least 12 hours, at least 24 hours, at least 30 hours, at least 36 hours, and at least 72 hours.

* * * * *